United States Patent [19]

Ripani

[11] Patent Number: 4,519,304

[45] Date of Patent: May 28, 1985

[54] DEVICE FOR CONTROLLING AND MONITORING THE THICKNESS OF A CHOCOLATE FILM DELIVERED BY CHOCOLATE REFINERS

[75] Inventor: Sergio Ripani, Milan, Italy

[73] Assignee: Carle & Montanari S.p.A., Milan, Italy

[21] Appl. No.: 574,275

[22] Filed: Jan. 26, 1984

[30] Foreign Application Priority Data

Apr. 21, 1983 [IT] Italy ............................. 20718 A/83

[51] Int. Cl.³ ............................................. B02C 25/00
[52] U.S. Cl. ........................................ 99/489; 99/486; 100/47; 100/168; 241/37
[58] Field of Search .............. 99/474, 485, 516, 534, 99/452, 460, 487; 426/475, 486, 518, 629; 241/34, 36, 37; 100/47, 43, 68, 170; 425/172, 363, 367

[56] References Cited

U.S. PATENT DOCUMENTS

| | | | |
|---|---|---|---|
| 2,230,166 | 1/1941 | Skanes | 99/485 |
| 2,992,866 | 7/1961 | Cavalieri | 241/231 X |
| 3,423,938 | 1/1969 | Cavalieri | 60/534 |
| 4,117,054 | 9/1978 | Salo | 100/47 X |

*Primary Examiner*—Timothy F. Simone
*Attorney, Agent, or Firm*—Irving M. Weiner; Pamela S. Burt

[57] ABSTRACT

A device for controlling and monitoring the thickness of a chocolate film delivered by chocolate refiners. The chocolate film thickness is controlled by operation of a roller bearing pressure adjustment system of the refiner by way of cut-in signals from an indirect measurement of the instantaneous chocolate film thickness effected by processing representative colorimetric signals for a given mass of chocolate stock of corresponding thickness values emitted by a readout head. The readout head is arranged to reciprocate to measure the film across its entire width. The readout head also enables the integrity of the chocolate film being delivered to be monitored, that is to detect the appearance on the output roller of dry band areas.

In the presence of potential causes of refiner roller seizure, the device, after a presettable time delay, will automatically stop the machine.

17 Claims, 5 Drawing Figures

DEVICE FOR CONTROLLING AND MONITORING THE THICKNESS OF A CHOCOLATE FILM DELIVERED BY CHOCOLATE REFINERS

BACKGROUND OF THE INVENTION

This invention relates to a device for controlling and monitoring the thickness of a chocolate film delivered by chocolate refiners.

As is known in the art, chocolate refiners are machines which comprise essentially a plurality of rollers successively carried for adjustable displacement to and from each other in a supporting frame or stand, to permit the gap between any one roller and the following roller to be adjusted. In this respect, the roller push-aside gap that the material being entrained may create decreases gradually from the input roller pair, arranged side-by-side to form an input chamber, and the last roller pair in the refiner, the last roller being the output or delivery roller. The delivery roller is wrapped over most of its circumference, e.g., ¾ of its circumference, with the chocolate film being delivered, which will leave said roller onto a doctoring blade associated with the delivery roller. The required chocolate film thickness may vary within a wide range, in general values of 15 to 30 $\mu$m being those required. Thus, the thickness dimensions handled are very small ones, and are dependent on the thickness dimensions of solid particulates of cocoa, sugar, milk, etc. contained in the film, which comprises, in a conventional manner, a mixture of cocoa, sugar, fatty substance or cocoa butter, milk, and so on. It will be apparent that this mixture is a heterogeneous one through the film of chocolate being delivered, the distribution of the individual ingredients per surface area unit occurring differently and irregularly in a random fashion. With prior refiners, the rollers which are located downstream of the input roller pair have a velocity which increases toward the output roller. This results in a squeezing and entraining action being applied on the chocolate mass to form a filn of decreasing thickness toward the output roller.

In order to resist undesired thickness deviations in the chocolate film being delivered, prior refiners provide for the bearing pressure therebetween to be changed, more specifically the bearing pressure from the input pair to the rollers downstream thereof. This may be achieved substantially in either of two ways, namely, by changing the bearing pressure on all the bearings of the refining rollers, or alternatively, by changing the bearing pressure on individual bearings of said refining rollers, the latter approach enabling the bearing pressure to be varied individually between the rollers. In all cases, the main adjustment is effected on the input roller pair, because, with the refiner in a steady state of operation, the amount per unit of time of the chocolate mass being fed must correspond to the amount by weight of the film being delivered.

No detailed description of the roller bearing pressure adjustment systems in such refiners will be given herein, because the device of this invention may be equally useful with any such pressure adjustment systems.

With all of the conventional refiners, irrespective of the more or less sophisticated construction of such systems for adjusting the pressure acting on the bearings of the refining rollers, the problem is encountered of how to measure the actual thickness of the film of chocolate being delivered. That measuring faculty is, however, much needed since a uniform thickness of the chocolate film is indispensable to subsequent processing thereof.

But since it is not possible to measure the chocolate fillm thickness in any direct manner, on account of the film having, on the one side, a very thin slurry-like consistency, and on the other side being kept moving onto a transporting surface (roller), it is current practice to check the thickness or fineness of the chocolate film in the laboratory by using a set of sifters in accordance with coded standards by OICC. However, the latter approach is far from satisfactory, because, on the one hand, it does not afford continuous measuring, and on the other hand, it yields measurement results only after a considerable time on the order of several hours. In fact, at production plants, such laboratories are usually located remote from the production areas, and completion of the measuring operations is time-consuming. Further, in the event of the results requiring an adjustment operation, even after such an adjustment has been carried out—mostly in an empirical fashion—a cross-checking measurement is to be taken again to assess the successful operation. Since such corrections require a number of operations, it will be appreciated that the correction time is quite a long one, while large amounts of chocolate are produced in the meantime which have a different fineness from the nominal or desired fineness.

With conventional refiners, moreover, supervision by an operator becomes necessary to prevent the appearance of solid fragments, such as the so-called "milk patches", or any small pieces of dried fruit shells accidentally dropped into the chocolate paste being fed from resulting in well-known serious seizing of the refiner. Such solid particles, in fact, would come to contact the feeder rollers, and unless taken in and passed over, would lay against the rollers and form an obstruction to the admission of the product onto the rollers with attendant formation thereon of peripheral band areas of absent product, and accordingly dry, which may be several millimeters wide. At such "dry" band areas the rollers are rapidly heated, thus leading to local expansion thereat, said rollers being in mutual contact at said areas. This quickly results in additional heating due to the different roller velocities of rotation, and within a few minutes, in roller seizure.

SUMMARY OF THE INVENTION

It is a primary object of this invention to provide a device for chocolate refiners, which can afford automatic adjustment of the refiner roller bearing pressure to ensure a uniform thickness dimension for the chocolate film being delivered across its entire width thereof.

A further object of the invention is to provide a device as indicated, which can monitor the integrity of the chocolate film being delivered and control, upon detection of lack of integrity of the film, the operation of a safety arrangement or arrangement for the automatic protection of the machine.

The above primary object of this invention is achieved by a device for controlling and monitoring the thickness dimension of a chocolate film in chocolate refiners, characterized in that it comprises:

detector means adapted to detect colorimetric signals for the chocolate film being delivered;

means adapted to convert said colorimetric signals into digitally processable signals;

means of setting electronically processable reference signals indicative of corresponding values of rated thickness dimensions for the chocolate film being delivered, and means of processing and comparing the signals processed by the colorimetric signals and the settable reference signals, said processing and comparing means being effective to generate output signals functioning as operative signals for the adjustment circuit of the side bearings of refining rollers in the refiner, so as to produce corresponding displacement movements of said rollers to accommodate thickness variations in the chocolate film being delivered, such as may occur with respect to the preset rated thickness. Another embodiment of this device is characterized in that said means of detecting colorimetric signals for the chocolate film being delivered comprises a colorimeter-like device, and said means of converting the colorimetric signals into processable signals comprises an optical-digital transducer, whereby alternate sequences are supplied of colorimetric signals for the instantaneous color of the chocolate film being delivered and of a reference color. Another embodiment of this device is characterized in that said detector head in the form of a colorimeter is carried on a reciprocable means along the entire width of the chocolate film delivery roller, to scan the instantaneous color across the width of said film, or timely detect the presence of any "dry band areas" onto the delivery roller. Further embodiments of this invention are characterized by the features particularly pointed out in the claims.

This inventive concept makes use of the unexpected finding that there exists direct proportionality of the thickness dimensions of chocolate film (for a given mass or formulation thereof) to the overall color thereof at the same thicknesses.

FIG. 1 of the accompanying drawings shows, by way of example only, two graphs, illustrating the relationship between brightness (transmittance) and fineness of two different chocolate types at different thicknesses, and more precisely, the line A relates to bitter chocolate and line B to milk chocolate. The tests have been carried out on a Hunterlab colorimeter (a product of Hunter Associates Laboratory, Inc., Reston, Va., U.S.A.) and a grindmeter. As is known, the Hunterlab colorimeter yields a numeric value of brightness or transmittance, i.e., the reflection factor, in accordance with an international standard referred to a scale ranging form 0 (black) to 100 (white). Transmittance represents the differential between the amount of light impinging on a colored surface and the amount of light which that surface returns or reflects. The grindmeter had two grooves of depth ranging from 0 to 50 $\mu$m and 50 to 200 $\mu$m, respectively. The chocolate paste was coated in the plastic state at a temperature of 40° C. The grindmeter was then placed under the colorimeter and measurements were taken of the chocolate color shades corresponding to the various thickness values graduated on the grindmeter scale. By joining together the color-/thickness or fineness plots from each reading, the graphs shown are obtained. From these graphs, it may be noted that the thickness rate of increase is substantially proportional to the color intensity increase, and viceversa.

In order to take, in the application being considered, a measurement, albeit an indirect one, of the thickness of the chocolate film being delivered, across the full width thereof, according to the invention, there is provided a reciprocating readout procedure scanning the entire width of the refining rollers. This represents a very special advantage, in that during this measuring or checking procedure in a reciprocating mode, according to the invention, any presence of so-called "dry band areas" onto the output roller can be timely detected, which would otherwise result in roller seizure and consequent machine stoppage and serious damages thereof.

Another advantage of this invention resides in the simple way the readouts are used, as formed by colorimetric or optical signals, to generate control or operative signals and adjust the pressure at the refiner roller bearings.

Still another advantage of the proposed solution is that the refiner operation can be automated in a simple and reliable manner.

An additional advantage is that it becomes possible to store in memory a number of values corresponding to the different colors, i.e., thickness dimensions or fineness, of the chocolate films being delivered, so as to repeat or set the same as desired at some later time. With the solution proposed by the invention, it is also possible to provide centralized control, i.e., several refiners can be controlled simultaneously with one and the same device.

Advantageously, moreover, with the proposed device, adjustment operations of the pressure at the roller bearings are carried out several times within a preset time interval, whereafter, should it prove impossible to restore the chocolate film to its desired thickness, an automatic protection arrangement is brought into operation to prevent seizures in the refiner. Such operations will be effected, as an example, upon detecting the cited "dry band areas", where even the so-called opening of the rollers in the input roller pair is inadequate to remove the causes of the "dry band areas" detected. This represents an important safety factor in the operation of the machine, or measure of protection thereof, which does away with the need for an attending operator.

Yet another advantage of this invention is that correct and reliable operating conditions can be ensured, along with a simple and compact construction.

Further features, advantages, and details of the inventive device will be more clearly understood from the following description with reference to the accompanying drawings,

DESCRIPTION OF THE PREFERRED EMBODIMENTS

Figure 4:
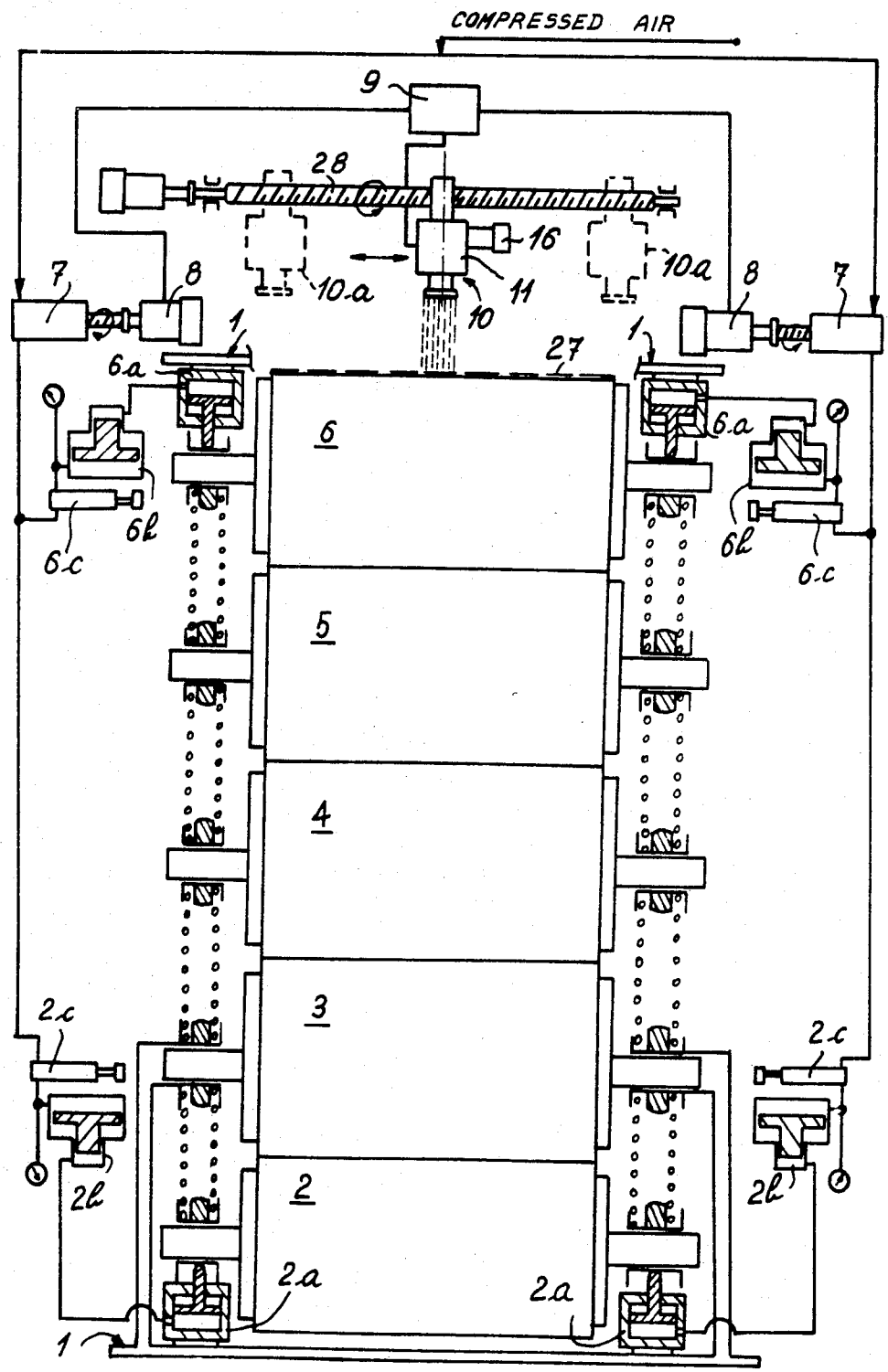
FIG. 4 is a front elevation view of a refiner incorporating a device according to the invention.
Figure 5:
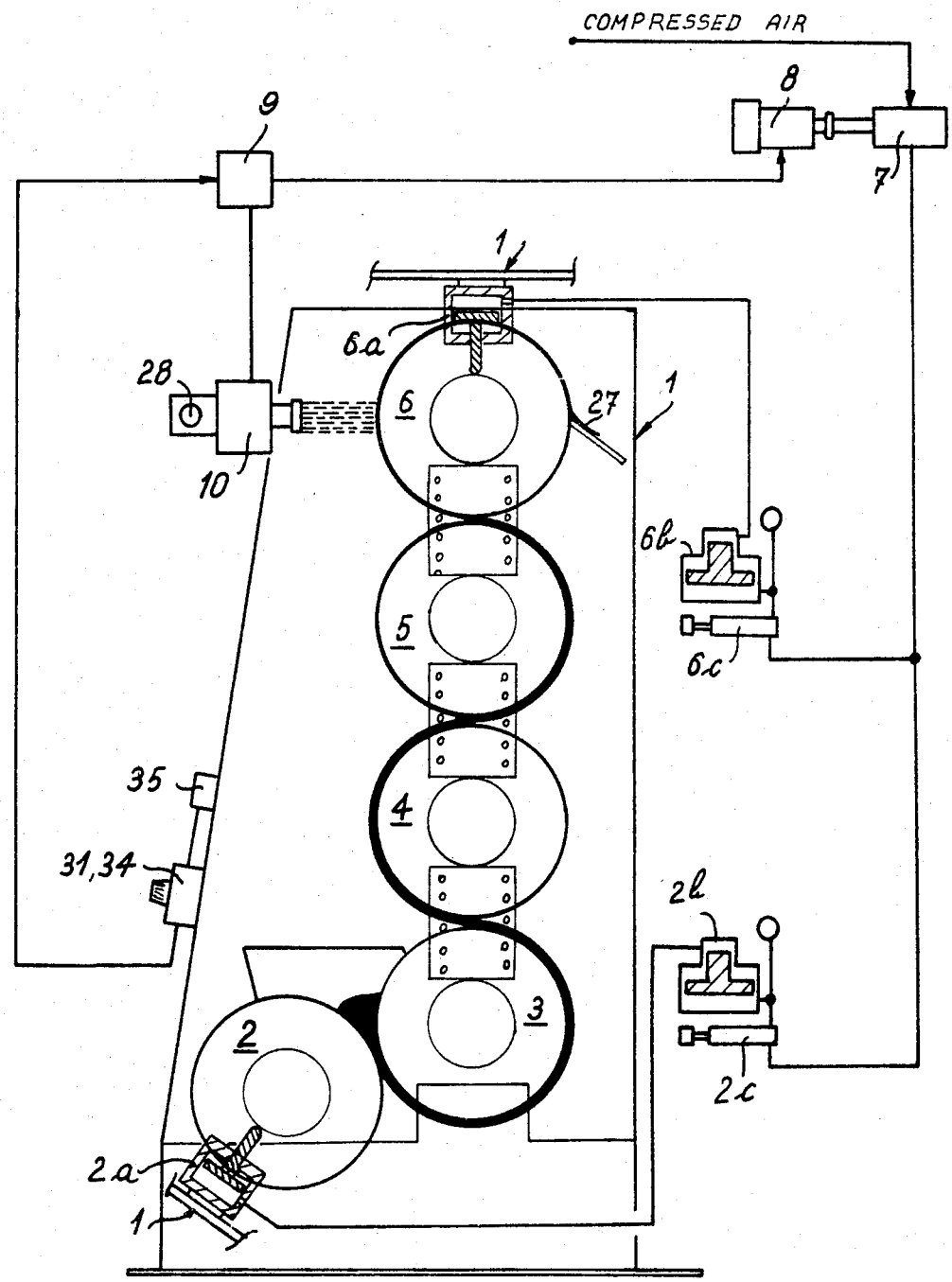
FIG. 5 is a side elevation view of the refiner of FIG. 4.

Throughout the drawing figures, similar parts are indicated with the same reference characters. As may be seen in particular in FIGS. 4 and 5, the refiner shown therein has a casing generally indicated at 1, which carries a plurality of refining rollers. In the example shown there are provided five such rollers, designated with the reference numerals 2 to 6. As diagramatically shown, the roller 3 is supported for rotation but not for translation, whereas the rollers 4 and 5 are supported springingly. Cylinder-piston assemblies 2a and 6a are associated on each side of the end rollers 2 and 6. The assemblies 2a and 6a can be actuated, for example, by way of pressure multiplier devices 2b and 6b, which are in turn associated with adjustment members 2c and 6c. The adjustment members 2c and 6c are included in a circuit of the pressure control system for controlling the pressure on the associated bearings, as shown in FIG. 4. Indicated at 7 are control actuators which are associated with a respective transducer or drive member 8. The latter are connected to the processing unit 9, which is, connected in turn to the readout head 10. The same includes, within a casing 11, a colorimetric portion 12 (FIGS. 2 and 3) and a transducer 13 for converting optical, i.e., colorimetric, signals into electric signals.

This will be more fully explained hereinafter.

The casing 11 is formed with an opening 14 and on the interior thereof there is carried a slit disk 15, e.g., in the form of a Maltese cross disk, which is driven by motor 16 through a drive 17. The casing 11 further accommodates a light source 18, advantageously in the form of a light bulb, powered by means of a feeder 19. Indicated at 20 is an emitted light concentrating and directing parabola element, and at 21 a diaphragm having a center aperture 22. Within the casing 11 there is also provided a lens 23. In the example shown, the casing 11 also comprises a side portion 24, which accommodates the optical-to-electric transducer 13 therein. The latter is advantageously in the form of a photodiode. As may be noted in FIGS. 2 and 3, the side portion 24 extends from the casing 11 at an inclination angle of approximately 45° C. and accommodates, in the example shown, a lens 25 and a filter 26.

In order to measure the thickness of the produced chocolate film 27 across its entire width thereof, the readout head 10 is mounted on reciprocating motion means. In the example shown, the readout head 10 is mounted on a worm 28, (FIGS. 4 and 5) supported and rotatively actuatable in a manner known per se. The same further includes a travel limit means, not shown, whereby the readout head 10 can occupy either end-of-travel position, or movement reversal position, as indicated at 10a (FIG. 4).

Figure 1:
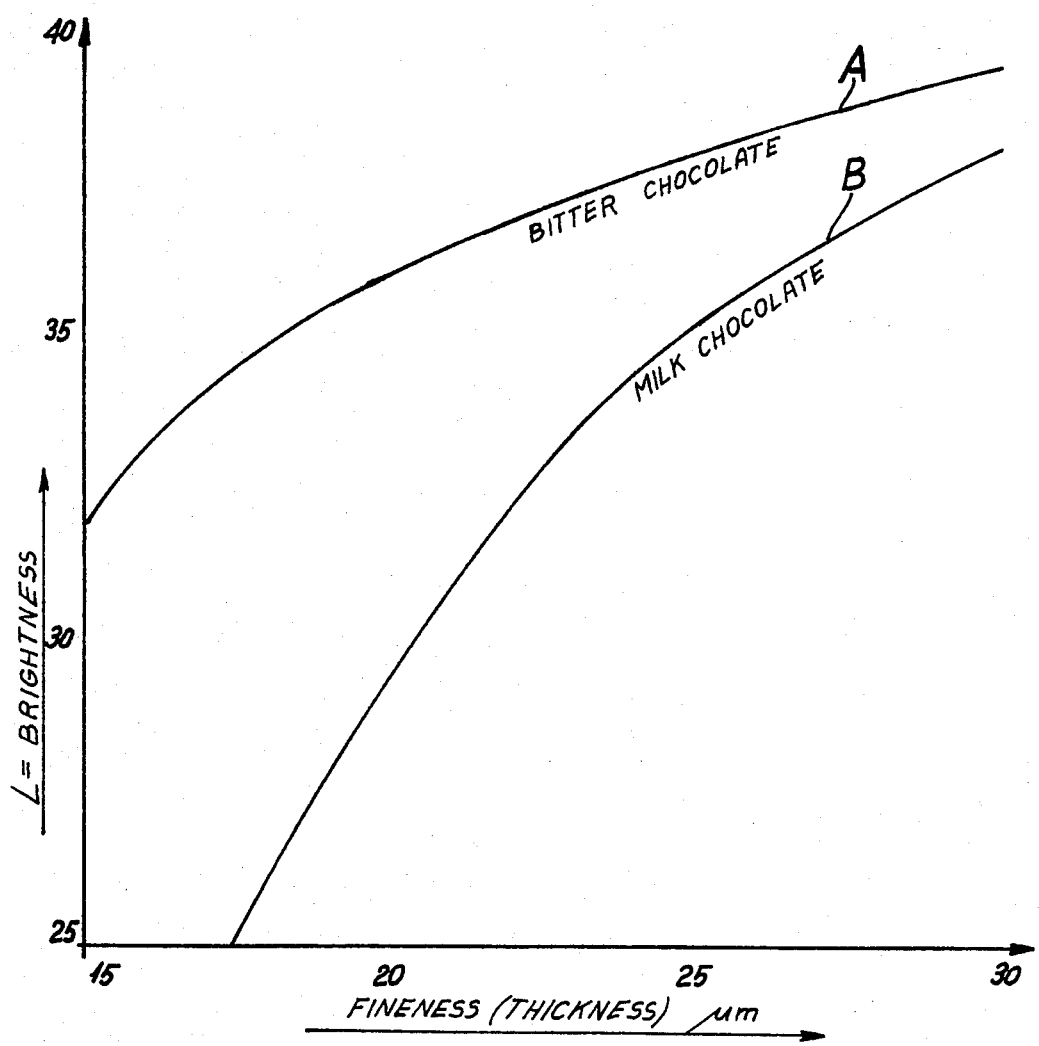
FIG. 1 is a graph including two plottings evidencing the proportional relationship existing between the color and thickness of a chocolate film, and specifically, a plotting or curve A for bitter chocolate, and a plotting or curve B for milk chocolate, the brightness values appearing on the ordinate axis, and the fineness or thickness values on the abscissa axis in $\mu$m.
Figure 2:
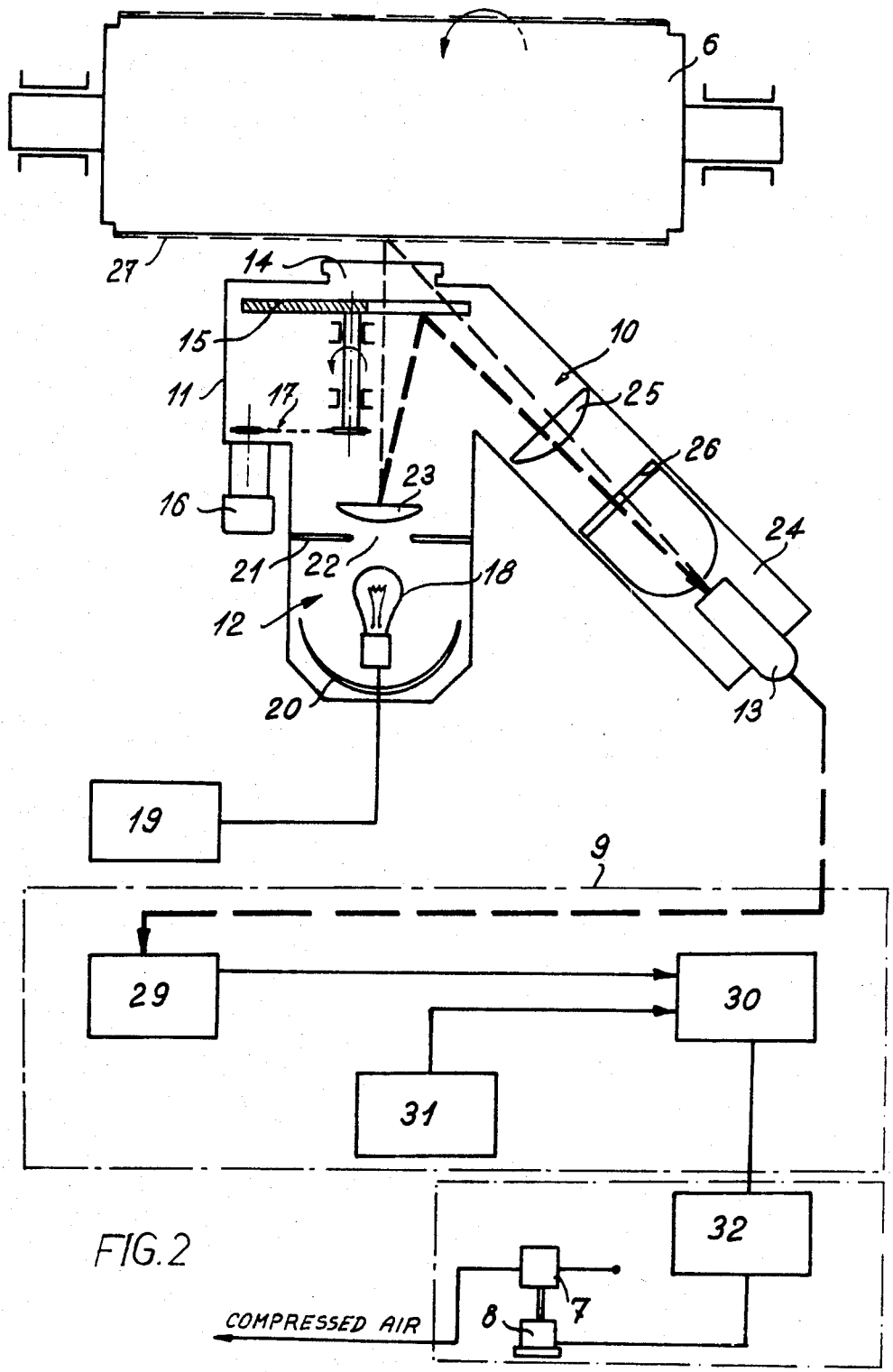
FIG. 2 is a general view of the inventive device according to an embodiment thereof providing for manual operation.

The processing unit 9 shown in FIG. 2 for manual operation comprises a signal ratio forming device 29, a signal comparing device 30, as well as a device 31 for manually setting digital values which correspond to the specific thickness desired each time for the chocolate film 27. Indicated at 32 is a transducer for converting signals from digital to analog, that is, into control signals for adjusting the pressure at the desired bearings of the refiner rollers, through the control members 8 associated with the actuators 7. The transmission of the pressure control signals on the actuator(s) of the refiner right-hand side and/or left-hand side will take place through the use of a switch (—not shown—), which produces such transmission in accordance with the positioning of the readout head 10 either on the right half or left half of the machine.

Figure 3:
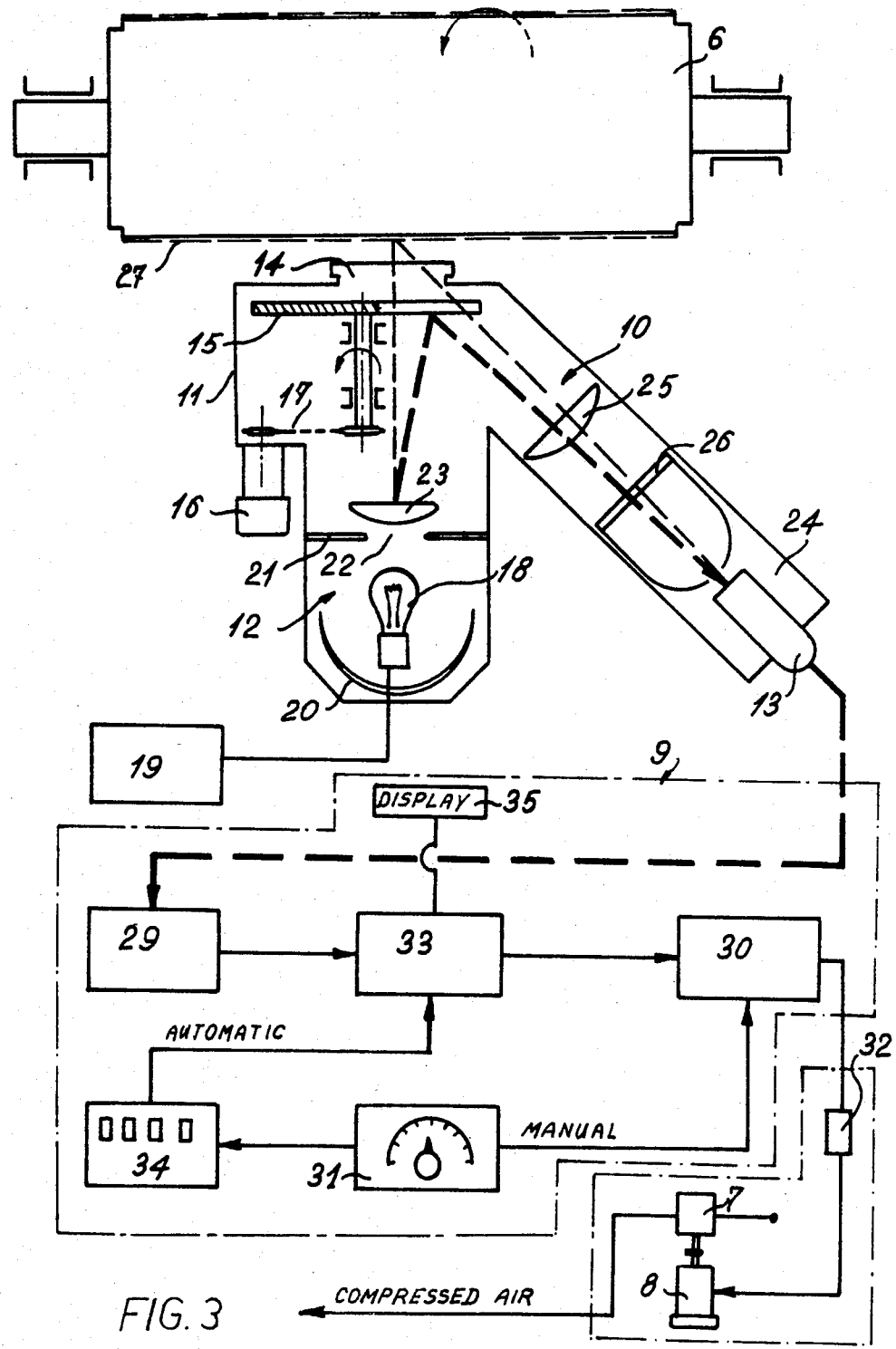
FIG. 3 is a similar view to FIG. 2, relating to an embodiment of the inventive device providing for automatic and centralized operation.

The processing unit 9 shown in FIG. 3, i.e., for automatic centralized operation, also comprises a microprocessor 33 and a keyboard 34 or the like, for inputting the automatic processing cycle each time desired. Indicated at 35 is a display unit.

The operation of the proposed device will now be described briefly.

The light emitted by the lamp 18 will impinge, after passing through the slit 22 and lens 23, both on the lower surface of the solid sectors of the Maltese cross disk 15, carrying a reference chocolate color, and on the outer surface of the chocolate film 27 being delivered on the roller 6. Thus, there are formed two alternate light beams, formed respectively by the light beam reflected from the bottom of the Maltese cross disk 15 and by the light beam reflected from the chocolate film 27. The two light beams form, accordingly, colorimetric or optical signals having the one a reference wavelength and the other a wavelength which is a function of the the average general color of the chocolate film 26 being delivered. After going through lens 25 and filter 26, in the example shown, said optical signal sequences reach the photodiode 13 which, following conversion of the optical signals into electric signals, passes them to the device 29 for forming the ratio of such signals and digitalizes them. Carrying out that ratio is advisable to avoid disturbance due to light fluctuations, and in that way, the signal/noise ratio is also improved through the numeric filtering technique. The signal level thus obtained is supplied to the comparator device 30, wherein said signals are compared with the level set manually by the operator on the manual setting device 31 corresponding to the desired operation condition, that is, the desired thickness dimension, for the chocolate film 27 delivered. If the levels to be compared in the comparator device 30 happen to coincide, that means that the thickness of the chocolate film 27 coincides with the desired rated value. Should the two signals differ, then a signal is emitted which, through the digital/analog conversion transducer 32, will supply control signals to operate the drive members 8, and hence, the actuators 7, or the control elements 2c,6c acting on the corresponding feed-in roller pair 2,3. In the presence of a lower measured thickness than the rated thickness, the pressure on the bearings of these rollers will be decreased, to allow the supply of an increased amount of chocolate paste, which will reflect in an increase of the film final thickness. In the event that excessively high thickness dimensions are measured, the pressure on the bearings of said rollers will be increased, with consequent reduction in the amount of chocolate delivered, and therefore, in the thickness of the resulting film. The control signals may be utilized as desired also to act on other bearings of the refining rollers, depending on the method of adjusting the pressure at the rollers considered in each case.

In the automatic operation mode with the microprocessor 33, FIG. 3, the latter is interposed between the device 29 for forming the signal ratio and comparator device 30, on the one side, and on the other side, the cited keyboard 34, which is in turn connected to the manual setting device 31. After the signals from the optical/electric transducer 13 have been digitalized and processed by means of the microprocessor 33, at the comparator device 30 there is carried out the comparison of said processed signals with the value set by the operator on the manual setting device 31, in a corresponding way to the thickness desired for the chocolate film 27. Where the value from the ratio forming device 29 and the value set on the device 31 happen to coincide, then an electric signal is generated and supplied to the microprocessor device 33 through the keyboard 34. Thus, from now onwards, the machine will operate automatically in a "hooked" fashion to the microprocessor device 33 and to the colorimetric/electronic signals from the readout head 10. The final processing of the processed signals into pressure control signals occurs similarly to the above procedure for manual adjustment. With the microprocessor embodiment, it becomes possible to store more data relating to the colors, and hence, to the desired thickness dimensions, thus the control of a number of refiners producing chocolate films with the same thickness may be centralized by the proposed device. The manual setting embodiment will involve, in all cases, considerably lower production costs.

It should be noted that the value set on the keyboard 34 corresponds to a certain predetermined value, and accordingly, to the related fineness or thickness, and the same is stored and is, therefore, advantageously repeatable as desired in time. Thus, processing cards may be issued which enable production of the required range of thicknesses of the chocolate film.

It should be further noted that the thickness correction operation, is advantageously carried out several times within a short predetermined time lapse, irrespective of the causes of thickness variation or of film interruptions. This expedient has the effect that if during the control operation period the film uniformity cannot be restored, then the proposed device will bring the refiner to a stop, to avoid any seizures. In operation, the device, in addition to controlling the pressure between the refining rollers to achieve the desired thickness in the delivered film, also monitors on an equally continuous basis the film continuity or integrity.

In addition, to the mode of operation described hereinabove, the invention also provides for a more sophisticated operation thereof in the event that dry band areas are on the delivery roller are detected.

In the presence of said dry band areas, the reader immediately recognizes them as such, because it reads directly the color of the surface of the delivery roller, that is, a color the assessment and measurement of which clearly lay out of the control range of the optical reader. Thus, it will issue a particular end-of-scale signal, which in this embodiment will be utilized as follows. Through the time elapsing from the first to the second detection of the dry band area, the device is still inactive, since it sometimes occurs that the solid piece causing the dry band area is ejected from the feed-in rollers without any further action. If however, on the second detection of the dry band area, that is, during the return stroke of the readout head, that dry band area persists, then timely steps are taken to determine a maximal decrease of the pressure on the bearings of the adjustable feed-in rollers, that is, the gap between the input rollers is maximized, as well as between the other rollers, if necessary, to facilitate the ejection of the solid pieces from the machine. If this does not occur within a short, settable time, further steps are taken to determine, as with the simpler mode of operation, a machine stop and avoid seizure failures therein. Thus, the device also performs an effective action of automatic protection of the refiner. The devices required for that purpose, i.e., timer and halting means, as well as advantageously of visual or acoustical warning, are no further illustrated because selectable as desired and within the capabilities of a skilled person in the art.

It may be appreciated from the foregoing that the proposed device effectively solves the problem on which this invention is based, and affords the advantages cited in the preamble.

Thus, according to the invention, of substantial import is the use of the refiner roller control to achieve, or maintain, the rated thickness for the chocolate film, through the use of an indirect "measurement" of said thickness dimension, i.e., by measuring the film color. Also substantial is the provision of the reciprocable readout head along the length of the delivery roller.

In practicing the invention, all of the individual parts may be replaced with other technically and/or functionally equivalent parts. As an example, the colorimeter structure may be readily replaced with other similar devices, such as ones having a reference color plate supported for a reciprocating motion instead of the Maltese cross disk, and so on, without departing from the protection scope of the instant invention.

Also contemplated by this invention is the replacement of the processing parts, that is the above-mentioned transducers, with other functionally equivalent devices, it remaining substantial to the invention the concept of processing colorimetric signals to generate control signals of adjustment of the pressure.

While thickness values of 15 to 30 $\mu$m have been mentioned, it will be apparent that the proposed device may also be used with thickness dimensions other than the indicated ones, as well as on other machines, or in other fields posing a comparable problem, such as the field of paints, inks, etc.

All of the features to be inferred from the specification, claims and drawings are regarded as substantial to this invention, both individually and in any combinations thereof.

I claim:

1. A device for controlling and monitoring the thickness dimension of a chocolate film in a chocolate refiner, comprising:
   detector means for detecting colorimetric signals for the film being delivered;
   means for converting said colorimetric signals into digitally processable signals;
   means for setting electronically processable reference signals indicative of corresponding values of rated thickness dimension for the chocolate film being delivered; and
   means for processing and comparing the signals processed by the colorimetric signals and the settable reference signals, said processing and comparing means being effective to generate output signals functioning as operative signals for an adjustment circuit of the side bearings of refining rollers in said chocolate refiner to produce corresponding displacement movements of said rollers to vary the thickness of the chocolate film being delivered in accordance with the preset rated thickness.

2. A device according to claim 1, wherein:
   said detector means comprises a colorimeter-like device; and
   said means for converting said colorimetric signals into digitally processable signals comprises an optical-digital transducer, whereby alternate sequences of colorimetric signals are supplied for the instantaneous color of the chocolate film being delivered and of a reference color.

3. A device according to claim 1, wherein:

said detector means includes a detector head in the form of a colorimeter, and said detector head is carried on a reciprocal means along the entire width of a chocolate film delivery roller to scan the instantaneous color across the width of said chocolate film and timely detect the presence of any dry band areas.

4. A device according to claim 2, wherein:

said detector means includes a detector head in the form of a colorimeter, and said detector head is carried on a reciprocal means along the entire width of a chocolate film delivery roller to scan the instantaneous color across the width of said chocolate film and timely detect the presence of any dry band areas.

5. A device according to claim 1, wherein:

said means for processing and comparing the signals processed by the colorimetric signals and the settable reference signals comprises a divider device and a comparator device;

said divider device effects the ratio signal sequences from the colorimetric signals/processable signal transducer;

and said comparator device carries out a comparison between the signals from said divider device and a reference value to be set by the operator on a predetermined value setting device and indicative of the desired rated thickness dimension; and the output signals from said comparator device function as operation signals acting on the adjustment devices provided in the control system for the bearings of the refiner rollers.

6. A device according to claim 5, including:

a microprocessor operably connected between said device for forming the ratio of the signal sequences from the colorimetric/processable signal transducer and the comparator device; and an intervening keyboard device operably connected to said microprocessor for supplying said microprocessor with an output from said device for manually setting set values indicative of the preset rated thickness values.

7. A device according to claim 1, including:

a transducer or signal amplifier device is operably interposed between the device for comparing the process signals and set signal, and the device controlled through the generated control signals.

8. A device according to claim 1, including:

a timer device adapted to establish a time limit for effecting adjustment operations on the refiner rollers, when film thickness values persist which deviate from the rated one, or in the presence of discontinuities of the film thickness values beyond said time limit, for stopping said refiner.

9. A device according to claim 1, including:

circuit and operative means causing, upon detection of the presence of dry band areas, a movement of maximum decrease of the pressure at the bearings of the adjustable roller in the input roller pair, as well as at the bearings of the other refining rollers to thereby permit the ejection of solid matter causing the detected dry band areas, and after a settable time duration to stop said refiner when said dry band areas persist.

10. A device according to claim 1, including:

a change-over switch operative to cause the control signals for the refiner roller pressure to be passed individually to either side of the adjustment system in accordance with the detection of thickness or colorimetric values which deviate from the rated value along the right or left half length with respect to the refiner centerline.

11. A device according to claim 2, wherein:

said colorimeter-like device includes a light source, a Maltese cross disk allowing light through the openings thereof, and a reference color on the undersurface thereof, such reference color being the average color of chocolate;

there is provided means for rotating said Maltese cross disk; and said detector means includes a lens and a filter at the derived output portion for the colorimetric signals.

12. A device according to claim 1, wherein:

the control signals acting on the bearings of the refiner rollers are caused to act on the bearings of either roller in chocolate paste input roller pair.

13. A device according to claim 1, wherein:

pressure control signals for the refiner roller bearings are also caused to act on the bearings of one or more of the other refining rollers, as well as on said one roller in the input roller pair.

14. A device according to claim 6, wherein:

said microprocessor contained in the processing portion for the readout signals of the temporary thickness as a function of the actual measurement of the instantaneous color of the chocolate film being delivered, is connected to a computer.

15. A chocolate refiner comprises:

first means for detecting the thickness of a chocolate film as well as for monitoring the integrity thereof;

signal processing means operably and electrically connected to said first means;

adjustment means operably and electrically connected to said signal processing means;

said adjustment means being operative to adjust the thickness and integrity of said chocolate film upon receiving predetermined adjustment control signals from said signal processing means; and said signal processing means receiving signals generated by said first means and converting such generated signals into said adjustment control signals.

16. A chocolate refiner according to claim 15, wherein:

said first means includes an indirect readout device for thickness of a chocolate film being delivered, as well as for monitoring the integrity thereof.

17. A device according to claim 2, wherein said thickness dimension for the chocolate film being delivered is within the range of 15 to 30 microns.

* * * * *